United States Patent [19]
Galbo et al.

[11] Patent Number: 5,844,026
[45] Date of Patent: Dec. 1, 1998

[54] N,N',N''-TRIS{2,4-BIS[HYDROCARBYLOXY-2,2,6,6-TETRA-METHYLPIPERIDIN-4-YL)ALKYLAMINO]-S-TRIAZIN-6-YL}-3,3'-ETHYLENEDIIMINODIPROPYLAMINES, THEIR ISOMERS AND BRIDGED DERIVATIVES AND POLYMER COMPOSITIONS STABILIZED THEREWITH

[75] Inventors: James P. Galbo, Wingdale, N.Y.; Henry C. Grace, Satsuma, Ala.; Douglas W. Horsey, Briarcliff Manor, N.Y.; Peter Solera, Suffern, N.Y.; Rangarajan Srinivasan, Tarrytown, N.Y.

[73] Assignee: Ciba Specialty Chemicals Corporation, Tarrytown, N.Y.

[21] Appl. No.: 885,613

[22] Filed: Jun. 30, 1997

[51] Int. Cl.$^6$ .................. C08K 5/3435; C07D 403/00
[52] U.S. Cl. .................. 524/100; 524/91; 524/101; 524/102; 524/120; 524/126; 524/153; 524/291; 524/310; 524/359; 524/394; 524/432; 524/198; 252/403
[58] Field of Search .................. 252/403; 524/100, 524/91, 101, 102, 120, 126, 153, 291, 310, 359, 394, 432; 544/198

[56] References Cited

U.S. PATENT DOCUMENTS

| | | | |
|---|---|---|---|
| 4,204,473 | 5/1980 | Winter et al. | 546/188 |
| 4,259,467 | 3/1981 | Keogh et al. | 526/279 |
| 4,325,863 | 4/1982 | Hinsken et al. | 524/94 |
| 4,335,147 | 6/1982 | Deichert et al. | 526/264 |
| 4,338,244 | 7/1982 | Hinshen et al. | 524/109 |
| 4,921,962 | 5/1990 | Galbo et al. | 546/184 |
| 5,004,770 | 4/1991 | Cortolano et al. | 524/99 |
| 5,015,682 | 5/1991 | Galbo | 524/102 |
| 5,096,950 | 3/1992 | Galbo et al. | 524/99 |
| 5,112,890 | 5/1992 | Behrens et al. | 524/95 |
| 5,124,378 | 6/1992 | Behrens et al. | 524/95 |
| 5,175,312 | 12/1992 | Dules et al. | 549/307 |
| 5,204,473 | 4/1993 | Winter et al. | 546/189 |
| 5,216,156 | 6/1993 | Galbo et al. | 544/198 |

FOREIGN PATENT DOCUMENTS 0309402  3/1989  European Pat. Off. .

*Primary Examiner*—Kriellion S. Morgan
*Attorney, Agent, or Firm*—Luther A. R. Hall

[57] ABSTRACT

A mixture of the compounds identified in the title, their pure isomers and alkane-bridged derivatives are particularly effective in stabilizing polymer compositions, particularly polyolefin compositions.

32 Claims, No Drawings

N,N',N''-TRIS{2,4-BIS[HYDROCARBYLOXY-2,2,6,6-TETRA-METHYLPIPERIDIN-4-YL) ALKYLAMINO]-S-TRIAZIN-6-YL}-3,3'-ETHYLENEDIIMINODIPROPYLAMINES, THEIR ISOMERS AND BRIDGED DERIVATIVES AND POLYMER COMPOSITIONS STABILIZED THEREWITH

The general invention pertains to selected N,N',N'''-tris [2,4-bis[(1-hydrocarbyloxy-2,2,6,6-tetramethylpiperidin-4-yl)alkylamino]-s-triazin-6-yl]-3,3'-ethylenediiminodipropylamines, their pure isomers, and bridged derivatives and to polymer compositions stabilized therewith.

The instant compounds, because of their low basicity, are of particular value in the stabilization of polymer compositions where the activity of more basic hindered amine stabilizers is significantly reduced because of interaction with the polymer substrate. Examples of polyolefin compositions in which the instant compounds are particularly effective include flame-retardant polyolefins where acidic residues from the decomposition of halogenated flame retardants deactivate normal hindered amine stabilizers, greenhouse films and agricultural mulch films where acidic residues from pesticides interfere with the activity of normal hindered amine stabilizers, and thermoplastic polyolefins where interactions with basic hindered amine stabilizers interfere with painting the substrate.

BACKGROUND OF THE INVENTION

N,N',N'',N'''-Tetrakis substituted hindered amines, which are described by formula I where $R_1$–$R_4$ are all E, have been patented as less basic, non-interacting polymer stabilizers in various ambient and thermoset automotive coatings, polyolefin, and non-polyolefin applications as taught in U.S. Pat. Nos. 5,004,770; 5,096,950; 5,204,473; 5,112,890 and 5,124,378; and in European Patent Application 309402 A1. Specifically, the preparation of N,N',N'',N'''-tetrakis{2,4-bis[(1-cyclohexyloxy-2,2,6,6-tetramethylpiperidin-4-yl) butylamino]-s-triazin-6-yl}-3,3'-ethylenediiminodipropylamine and its octyloxy analogue is described by Winter et al., respectively, in Examples 62 and 67 of U.S. Pat. No. 5,204,473. The same patent also claims the 1-methoxy analogue in claim 25. None of the above patents contain any specific performance data on these tetra-substituted-s-triazine hindered amine stabilizers in any organic substrate.

The instant invention differs from the prior art in that the instant compounds have one unsubstituted nitrogen on the tetraamine backbone. Furthermore, none of the prior art, including U.S. Pat. No. 5,015,682, which describes oligomeric N-hydrocarbyloxy hindered amine stabilizers, discloses the bridged structures described by formulae II and III.

DETAILED DISCLOSURE

The instant invention pertains to a mixture of N,N',N'''-trisf{2,4-bis[(1-hydrocarbyloxy-2,2,6,6-tetramethylpiperidin-4-yl)alkylamino]-s-triazin-6-yl}-3,3'-ethylenediiminodipropylamine; N,N',N''-tris{2,4-bis[(1-hydrocarbyloxy-2,2,6,6-tetramethylpiperidin-4-yl) alkylamino]-s-triazin-6-yl}-3,3'-ethylenediiminodipropylamine, and bridged derivatives as described by formulas I, II, IIA and III $R_1NH$—$CH_2CH_2CH_2NR_2CH_2CH_2NR_3CH_2CH_2CH_2NHR_4$ (I)

$T$—$E_1$—$T_1$ (II)

$T$—$E_1$ (IIA)

$G$—$E_1$—$G_1$—$E_1$—$G_2$ (III)

E is

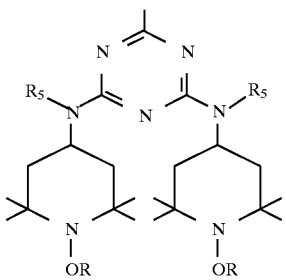

$E_1$ is

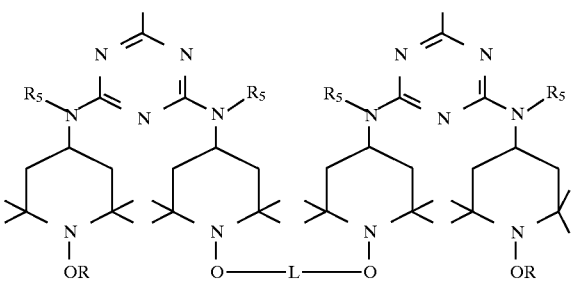

where in the tetraamine of formula I,
$R_1$ and $R_2$ are the s-triazine moiety E; and one of $R_3$ and $R_4$ is the s-triazine moiety E with the other of $R_3$ and $R_4$ being hydrogen,
R is methyl, cyclohexyl or octyl, preferably cyclohexyl or octyl,
$R_5$ is alkyl of 1 to 12 carbon atoms, preferably n-butyl;
where in the compound of formula II or IIA when R is cyclohexyl or octyl,
T and $T_1$ are each a tetraamine substituted by $R_1$–$R_4$ as defined for formula I, where
(1) one of the s-triazine moieties E in each tetraamine is replaced by the group $E_1$ which forms a bridge between the two tetraamines T and $T_1$, or
(2) the group $E_1$ can have both termini in the same tetraamine T as in formula IIA where two of the E moieties of the tetraamine are replaced by one $E_1$ group, or
(3) all three s-triazine substituents of tetraamine T can be $E_1$ such that one $E_1$ links T and $T_1$ and a second $E_1$ has both termini in tetraamine T,
L is cyclohexanediyl or octanediyl;
where in the compound of formula III
G, $G_1$ and $G_2$ are each tetraamines substituted by $R_1$–$R_4$ as defined for formula I, except that G and $G_2$ each have one of the s-triazine moieties E replaced by $E_1$, and $G_1$ has two of the triazine moieties E replaced by $E_1$, so that there is a bridge between G and $G_1$ and a second bridge between $G_1$ and $G_2$;
which mixture is prepared by reacting two to four equivalents of 2,4-bis[(1-hydrocarbyloxy-2,2,6,6-piperidin-4- yl)butylamino]-6-chloro-s-triazine with one equivalent of N,N'-bis(3-aminopropyl)ethylenediamine.

The compounds of formula I have two possible isomers assuming that there is no bridging between molecules. These two isomers are outlined in the table below.

| Isomer | $R_1$ | $R_2$ | $R_3$ | $R_4$ |
|--------|-------|-------|-------|-------|
| 1 | E | E | H | E |
| 2 | E | E | E | H |

The instant compounds are prepared by reacting 2–4 equivalents of a 2,4-bis[(1-hydrocarbyloxy-2,2,6,6-tetramethylpiperidin-4-yl)alkylamino]-6-chloro-s-triazine with 1 equivalent of N,N'-bis(3-aminopropyl) ethylenediamine in a hydrocarbon solvent with an acid acceptor, such as aqueous sodium hydroxide, used to neutralize the hydrochloric acid produced in the reaction. The synthesis of various 2,4-bis[(1-hydrocarbyloxy-2,2,6,6-tetramethylpiperidin-4-yl)alkylamino]-6-chloro-s-triazines is described in U.S. Pat. Nos. 5,216,156 and 5,204,473.

The preferred method for synthesis of the 2,4-bis [(1-hydrocarbyloxy-2,2,6,6-tetramethylpiperidin-4-yl) alkylamino]-6-chloro-s-trazines is to heat a mixture of the corresponding hindered amine substituted 6-chloro-s-triazine with tert-butyl hydroperoxide, a metal oxide catalyst, and the appropriate hydrocarbon solvent until the red color of the nitroxyl intermediate is discharged as taught in U.S. Pat. No. 4,921,962. In some instances, two nitroxyl radicals will couple with the same solvent molecule. This is the source of the bridged material depicted by formulae II and III as described above. The N-methoxy compounds of the instant invention do not contain these bridged structures because different synthetic methodology is used to generate 1-methoxy substituted hindered amines.

U.S. Pat. No. 5,204,473 describes the introduction of a 1-cyclohexyloxy or 1-octyloxy substituent on a tetra-substituted s-triazine hindered amine starting material. The instant tris-substituted compounds differ from the tetra-substituted compounds of prior art because they are prepared by a different route as shown below. Even with the use of 4 equivalents of the chloro-s-triazine intermediate, the majority of the product mixture is tris-substituted. The use of as little as 2 equivalents of the chloro-s-triazine intermediate still gives some tris-substituted product.

The instant invention also pertains to a composition stabilized against thermal, oxidative or light-induced degradation which comprises, (a) an organic material subject to thermal, oxidative or light-induced degradation, and (b) an effective stabilizing amount of a compound of formula I, II, IIA or III.

Preferably, the organic material is a natural, semi-synthetic or synthetic polymer, especially a thermoplastic polymer.

Most preferably, the polymer is a polyolefin or polycarbonate, especially polyethylene or polypropylene.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

In general polymers which can be stabilized include
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls, cycloalkenyl, cyclopentadienyl, and/or aryls that may be either π- or σ-coordinated. These metal complexes may be in the free form or supported on substrates, typically on activated magnesium chloride, titanium(III) chloride, alumina or silicon oxide. These catalysts may be soluble or insoluble in the pollmerisation medium. The catalysts can be used by themselves in the polymerisation or further activators may be used, typically metal alkyls, metal hydrides, metal alkyl halides, metal alkyl oxides or metal alkyloxanes, or compounds that afford non-coordinating anions such as tris(pentafluorophenyl)boron, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), constrained geometry catalyst technology CGCT (Dow), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl mnethacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymrers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose proplonates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.gr. natural latex or latices of carboxylated styrene/butadiene copolymers.

31. Polysiloxanes such as the soft, hydrophilic polysiloxanes described, for example, in U.S. Pat. No. 4,259,467; and the hard polyorg-anosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsat rate d monomers or oligomers and a polyunsaturated aliphatic oligomer.

34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, Such as the materials listed below, or mixtures thereof.

1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-((α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
1.7. Esters of β-(3,5-di-tert-butyl-4-hydroxyphenyl)-propionic acid with monohydric or polyhydric alcohols, for example,
methanol
octadecanol
diethylene glycol
triethylene glycol
1,6-hexanediol
neopentyl glycol
thiodiethylene glycol
triethanolamine
pentaerythritol
tris-hydroxyethyl isocyanurate
di-hydroxyethyl oxalic acid diamide
triisopropanolamine
1.8. Esters of β-(5-tert-butyl-4-hydroxy-3-methylphenyl)-propionic acid with monohydric or polyhydric alcohols, for example,
methanol
octadecanol
1,6-hexanediol
neopentyl glycol
thiodiethylene glycol
triethanolamine
diethylene glycol triethylene glycol
pentaerythritol
tris-hydroxyethyl isocyanitrate
di-hydroxyethyl oxalic acid diamide
triisopropanolamine 1.9. Amides of β-(3,5-di-tert-butyl-4-hydroxyphenyl)-propionic acid for example,
N,N'-di-(3,5-di-tert-butyl-4-hydroxyphenylpropion yl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and liaht stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-,3'-dodecyl-5'-methyl-, and 3'-tert-butyl-5'-(2-octyloxycarbonyl)ethyl-, and dodecylated-5'-methyl derivatives, and 3'-α-cumyl-5-tert-octyl.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, (α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1 ,2,2,6,6-pentamethylpiperidyl) sebacate, n-butyl-3,5-di-tert. butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetra-methylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone), bis (1-octyloxy-2,2,6,6-tetramethylpiperidin-4-yl) sebacate, N.N',N",N"'-tetrakis[4,6-bis(butyl-1,2,2,6,6-pentamethylpiperidin-4-yl)amino-s-triazin-2-yl]-1,10-diamino-4,7-diazadecane.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecyl-pentaerythritol diphosphite, di-(2,4,6-tri-tert-buitylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibuLtyl-dithiocarbamate, dioctadecyl dissulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecyl nitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleatina agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338,244 or U.S. Pat. No. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl).benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), UV absorbers (items 2.1 and 2.2 of the list), sterically hindered amines (item 2.6 of the list), phosphites and phosphonites (item 4 of the list) and hydroxylamines (item 6 of the list.

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamide), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis (4,6-di-tertbutylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis(amino-2,2,6,6-tetrimethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane)diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-(2,2,6,6-tetramethgypipegin-4-yl)-n-dodecylsuccinimide, N-(1,2,2,6,6-pentamethylpiperidin-4-yl)-n-dodecylsuccinimide, N-(1-acetyl-2,2,6,6-tetramethylpiperidin-4-yl)-n-dodecylsuccinimide, 1-acetyl-3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino]}, and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4- hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]1,10-diamino-4,7-diazadecane. di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)iminol]}, or 2,4,6-tris[N-(1-cyclohexyloxy-2,2,6,6-tetramethylpiperidin-4-yl)-n-butylamino]-s-triazine.

The instant invention also pertains to a process of making the instant mixture of N,N',N'''-tris{2,4-bis[(1-hydrocarbyloxy-2,2,6,6-tetramethylpiperidin-4-yl)alkylamino]-s-triazin-6-yl}-3,3'-ethylenediiminodipropylamine; N,N',N''-tris{2,4-bis-[(1-hydrocarbyloxy-2,2,6,6-tetramethylpiperidin-4-yl)alkylamino]-s-triazin-6-yl}-3,3'-ethylenediiminodipropylamine and bridged derivatives as described by formulas I, II, IIA and III defined supra which comprises reacting two to four equivalents of 2,4-bis[(1-hydrocarbyloxy-2,2,6,6-piperidin-4-yl)butylamino]-6-chloro-s-triazine with one equivalent of N,N'-bis(3-aminopropyl)-ethylenediamine.

Preferably, the process involves reacting 2.5 to 3 equivalents of the s-triazine with one equivalent of amine; most preferably three equivalents of the s-triazine to one equivalent of amine.

There are advantages of the instant tris-substituted compounds over the related tetra-substituted compounds of the prior art. The tert-butyl hydroperoxide oxidation-coupling reaction used to introduce the 1-cyclohexyloxy or 1-octyloxy group on the tetra-substituted s-triazine hindered amine causes significant chain scission of the tetraamine moiety resulting in by-products of lower molecular weight. This chain scission is eliminated in the preparation of the instant compounds because the 1-alkoxy group is introduced in the absence of the tetraamine backbone.

The following examples are for illustrative purposes only and are not to be construed to limit the scope of the instant invention in any manner whatsoever.

Coadditives found useful for use with the instant hindered amine compounds of formulas I, II, IIA and III are as follows:

Antioxidants:
neopentanetetrayl tetrakis(3,5-di-tert-butyl-4-hydroxyhydrocinnamate, (IRGANOX® 1010, Ciba Specialty Chemicals Corp.);
octadecyl 3,5-di-tert-butyl-4-hydroxyhydrocinnamate, (IRGANOX® 1076, Ciba Specialty Chemicals Corp.);
1,3,5-trimethyl-2,4,6-tris(3,5,-di-tert-butyl-4-hydroxybenzyl)benzene, (IRGANOX® 1330, Ciba Specialty Chemicals Corp.);
1,2-bis(3,5-di-tert-butyl-4-hydroxyhydrocinnamoyl) hydrazine, (IRGANOX® MD 1024, Ciba Specialty Chemicals Corp.);
calcium [bis(monoethyl 3,5-ditert-butyl-4-hydroxybenzyl)phosphonate], (IRGANOX® 1425, Ciba Specialty Chemicals Corp.);
1,3,5-tris(3,5-di-tert-butyl-4-hydroxybenzyl) isocyanurate, (IRGANOX® 3114, Ciba Specialty Chemicals Corp.);
1,3,5-tris(3-hydroxy-4-tert-butyl-2,6-dimethylbenzyl isocyanurate, (CYANOX® 1790, Cytec).

Phosphorus Compounds:
tris(2,4-di-tert-butylphenyl) phosphite, (IRGAFOS® 168, Ciba Specialty Chemicals Corp.);
bis(2,4-di-tert-butyl-6-methylphenyl) ethyl phosphite, (IRGAFOS® 38, Ciba Specialty Chemicals Corp.);
2,2',2''-nitrilo[triethyl-tris-(3,3',5,5'-tetra-tert-butyl-1,1'-biphenyl-2,2'-diyl) phosphite], (IRGAFOS® 12, Ciba Specialty Chemicals Corp.);
tetrakis(2,4-di-butylphenyl) 4,4'-biphenylenediphosphonite, (IRGAFOS® P-EPQ, Ciba Specialty Chemicals Corp.);
tris(nonylphenyl) phosphite, (TNPP®, General Electric);
bis(2,4-di-tert-butylphenyl) pentaerythrityl diphosphite, (ULTRANOX® 626, General Electric);
2,2'-ethylidenebis(2,4-di-tert-butylphenyl) fluorophosphite, (ETHANOX® 398, Ethyl Corp.)
2-butyl-2-ethylpropan-1,3-diyl 2,4,6-tri-tert-butylphenyl phosphite, (ULTRANOX® 641, General Electric).

Benzofuran-2-ones:
5,7-di-tert-butyl-3-(3,4-dimethylphenyl)-2H-benzofuran-2-one, (HP-136®, Ciba Specialty Chemicals Corp.).

Hydroxylamines:
N,N-dialkylhydroxylamine made by the direct oxidation of N,N-di(hydrogenated tallow)amine, (FS-042®, Ciba Specialty Chemicals Corp.).

Hindered amines:
bis(2,2,6,6-tetramethylpiperidin-4-yl) sebacate, (TINUVIN® 770, Ciba Specialty Chemicals Corp.);
the polycondensation product of 1-(2-hydroxyethyl)-2,2,6,6-tetramethyl-4-hydroxypiperidine and succinic acid, (TINUVIN® 622, Ciba Specialty Chemicals Corp.);
N,N',N'',N'''-tetrakis[4,6-bis(butyl-1,2,2,6,6-pentamethylpiperidin-4-yl)amino-s-triazin-2-yl]-1,10-diamino-4,7-diazadecane, (CHIMASSORB® 119, Ciba Specialty Chemicals Corp.);
the polycondensation product of 4,4'-hexamethylenebis (amino-2,2,6,6-tetra-methylpiperidine) and 2,4-dichloro-6-tert-octylamino-s-triazine, (CHIMASSORB® 944, Ciba Specialty Chemicals Corp.);
the polycondensation product of 4,4'-hexamethylenebis (amino-2,2,6,6-tetra-methylpiperidine) and 2,4-dichloro-6-morpholino-s-triazine, (CYASORB® 3346, Cytec);
2,2,6,6-tetramethylpiperidin-4-yl octadecanoate, (CYASORB® 3853, Cytec);
3-dodecyl-1-(1-acetyl-2,2,6,6-tetramethylpiperidin-4-yl)-pylnolidin-2,5-dione, (CYASORB® 3581, Cytec);
1,3,5-tris{N-cyclohexyl-N-[2-(2,2,6,6-tetramethylpiperazin-3-on-4-yl) ethyl]-amino}-s-triazine, (GOODRITE® 3150, B. F. Goodrich);
poly[methyl 3-(2,2,6,6-tetramethylpiperidin-4-yloxy) propyl]siloxane, (UVASIL® 299, Enichem);
the polycondensation product of 2,4-dichloro-6-(2,2,6,6-tetramethylpiperidin-4-yl)-butylamino)-s-triazine and 2,2'ethylene-bis{[2,4-(2,2,6,6-tetramethylpiperidin-4-yl)butyl-amino-s-triazin-6-yl] aminotrimethyleneamino}, (HA 88).

NOR hindered amines:
bis(1-octyloxy-2,2,6,6-tetramethylpiperidin-4-yl) sebacate, (TINUVIN® 123, Ciba Specialty Chemicals Corp.);

bis(1-octyloxy-2,2,6,6-tetramethylpiperidin-4-yl) adipate;

bis(1-cyclohexyloxy-2,2,6,6-tetramethylpiperidin-4-yl) adipate;

bis(1-cyclohexyloxy-2,2,6,6-tetramethylpiperidin-4-yl) sebacate;

1-cyclohexyloxy-2,2,6,6-tetramethylpiperidin-4-yl octadecanoate.

Flame retardants:

tris(3-bromo-2,2-bis(bromomethyl)propyl) phosphate, (PB 370®, FMC Corp.)

decabromodiphenyl oxide, (DBDPO);

ethylene bis-(tetrabromophthalimide), (SAYTEX® BT-93);

ethylene bis-(dibromo-norbornanedicarboximide), (SAYTEX® BN-451)

UV absorbers:

2-(2-hydroxy-3,5-di-α-cumylphenyl)-2H-benzotriazole, (TINUVIN® 234, Ciba Specialty Chemicals Corp.);

2-(2-hydroxy-5-methylphenyl)-2H-benzotriazole, (TINUVIN® P, Ciba Specialty Chemicals Corp.);

5-chloro-2-(2-hydroxy-3,5-di-tert-butylphenyl)-2H-benzotriazole, (TINUVIN® 327, Ciba Specialty Chemicals Corp.);

2-(2-hydroxy-3,5-di-tert-amylphenyl)-2H-benzotriazole, (TINUVIN® 328, Ciba Specialty Chemicals Corp.);

2-(2-hydroxy-3-α-cumyl-5-tert-octylphenyl)-2H-benzotriazole, (TINUVIN® 928, Ciba Specialty Chemicals Corp.);

2,4-di-tert-butylphenyl 3,5-di-tert-butyl4-hydroxybenzoate, (TINUVIN® 120, Ciba Specialty Chemicals Corp.);

2-hydroxy-4-n-octyloxybenzophenone, (CHIMASSORB® 81, Ciba Specialty Chemicals Corp.);

2,4-bis(2,4-dimethyphenyl)-6-(2-hydroxy-4-octyloxyphenyl)-s-triazine, (CYASORB® 1164, Cytec).

EXAMPLE 1

2-Chloro-4,6-bis[N-(1-cyclohexyloxy-2,2,6,6-tetramethylpiperidin-4-yl)butylamino]-s-triazine A mixture of 57.7 g (0.448 mol) of 70% aqueous tert-butylhydroperoxide, 250 ml of cyclohexane and 100 ml of saturated sodium chloride solution is agitated vigorously and the organic layer is then separated and dried over anhydrous magnesium sulfate. The drying agent is removed by filtration. The filtrate, 30.0 g (0.056 mol) of 2-chloro-4,6-bis[N-(2,2,6,6-tetramethylpiperidin-4-yl)butylamino]-s-triazine and 1.0 g of molybdenum trioxide are placed in a pressure bottle and heated at 130°–140° C. The reaction mixture quickly turns red and heating is continued till the red color is discharged. The reaction mixture is allowed to cool and solids are removed by filtration. The filtrate is concentrated under reduced pressure to give an oil which is purified by flash chromatography on silica gel to afford 30.3 g. (74% yield) of the title compound as a white glass.

Although the white glass is essentially the title compound, some minor amount of bridged material may also be present.

EXAMPLE 2

2-Chloro-4,6-bis[N-(1-octyloxy-2,2,6,6-tetramethylpiperidin-4-yl)butylamino]-s-triazine A mixture of 57.7 g (0.448 mol) of 70% aqueous tert-butylhydroperoxide, 340 ml of octane, and 50 ml of saturated sodium chloride solution is agitated vigorously, and the organic layer is then separated and dried over anhydrous magnesium sulfate. The drying agent is removed by filtration. One-half of the tert-butyl hydroperoxidea)ctane Solution is combined with 30.0 g (0.056 mol) of 2-chloro-4,6-bis[N-(2,2,6,6-tetramethylpiperidin-4-yl)butylamino]-s-triazine and 1.0 g of molybdenum trioxide and the mixture is heated at reflux. Water is collected in a Dean-Stark trap. Once the mixture turns red, the remaining tert-butyl hydroperoxide/octane solution is added over a three-hour period while the reaction mixture is maintained at reflux. The mixture is heated for an additional hour to discharge the red color. The reaction mixture is then cooled to room temperature and solids are removed by filtration. The filtrate is concentrated under reduced pressure to obtain an amber oil which is purified by flash chromatography on silica gel (40:1, heptane/ethyl acetate) to afford 32.7 g (74% yield) of the title compound as a colorless syrup.

Although the colorless syrup is essentially the title compound, a minor amount of bridged material may also be present.

EXAMPLE 3

Reaction of 2,4-bis[(1-cyclohexyloxy-2,2,6,6-piperidin-4-yl)butylamino]-6-chloro-s-triazine with N,N'-bis(3-aminopropyl)ethylenediamine A mixture of 6.4 g (37 mmol) of N,N'-bis(3-aminopropyl) ethylenediamine, 107.6 g (147 mmol, 4.0 equivalents) of 2,4-bis[(1-cyclohexyloxy-2,2,6,6-tetramethylpiperidin-4-yl) butylamino]-6-chloro-s-triazine, as prepared in Example 1, as a 70% solution in cyclohexane, and 31.0 g of 20% aqueous sodium hydroxide solution is heated at 160° C. for four hours. The reaction is cooled and diluted with 60 g of cyclohexane. The aqueous layer is removed, the organic layer is concentrated and water is added to precipitate the crude product. The solids are washed with water till neutral and dried to afford 102 g of product. Analysis: Although four equivalents of the 6-chloro-s-triazine are used per one equivalent of tetraamine, nmr analysis shows that on average only three triazinyl groups are attached to the amine backbone.

The product is a mixture of isomers including bridged compounds. The mixture can be separated by preparative chromatography into the pure components, particularly the two non-bridged formula isomers discussed earlier.

EXAMPLE 4

Reaction of 2,4-bis[(1-cyclohexyloxy-2,2,6,6-piperidin-4-yl)butylamino]-6-chloro-s-triazine with N,N'-bis(3-aminopropyl)ethylenediamine The procedure of Example 3 is repeated, except that 3.0 equivalents of 2,4-bis[(1-cyclohexyloxy-2,2,6,6-tetramethylpiperidin-4-yl)butylamino]-6-chloro-s-triazine are used and the reaction is carried out at 120° C. over nine hours.

Again, this product is a mixture of isomers including bridged compounds. Analysis by nmr shows that on average between 2.5 and three triazinyl groups are attached to the amine backbone.

The $T_g$ for this product is 104°–118° C. as measured by DSC.

EXAMPLE 4a

Compartive Example

The compound of Example 62 of U.S. Pat. No. 5,204,473 is prepared by reacting the hindered amine precursor (CHIMASSORB® 905, Ciba), having four substituted s-triazinyl groups attached to the 3,3'ethylenediiminodipropylamine backbone, with molybdenum trioxide and cyclohexane to form the corresponding 1-cyclohexyloxy compound. This compound is supposedly tetrasubstituted as based on the original CHIMASSORB® 905 starting material. However, nmr and GPC analyses indicate that under the reaction conditions considerable scission of s-triazinyl groups and the formation of unknown colored by-products may have occurred and that only two s-triazinyl groups may still be bonded to the amine backbone.

In order to distinguish the instant "trisubstituted" compound of Example 4 from this prior art compound of Example 62 of U.S. Pat. No. 5,204,473, here designated as Example 4a, the $T_g$ of each compound is determined by DSC, and each compound is subjected to DSC and TGA analyses.

| Compound of | Tg (°C.) | |
|---|---|---|
| Example 4a | 88–93 | |
| Example 4 | 104–118 | |
| | DSC Analysis* | |
| | Onset (°C.) | Peak (°C.) |
| Example 4a | exotherm 141 | 173 |
| | exotherm 220 | 292 |
| Example 4 | exotherm 228 | 228 |
| | exotherm 269 | 299 |
| | TGA Analysis** Temperature at | |
| | 2%  10%  wt loss, (°C.) | 50% |
| Example 4a | 171  260 | 321 |
| Example 4 | 254  285 | 385 |

*DSC scans (10° C./min to 350° C., 100 ml/min $N_2$, Al pans, ~10 mg)
DSC - Estimate of error, Enthalpy to ±10%; Temp. to ±2° C.
**TGA scans (10° C./min to 500° C., 100 ml/min $N_2$, Al pans, ~10 mg)
TGA - Estimate of error, Temp. to ±5° C.; Weight to ±0.5% absolute.

It is clear from these data that the instant compound of Example 4 made by a different procedure from the prior art compound of Example 62 of U.S. Pat. No. 5,204,473 is not the same material at all and that the instant compound of Example 4 is far more thermally stable than is the prior art compound of Example 62.

EXAMPLE 5
Reaction of 2,4-bis[(1-cyclohexyloxy-2,2,6,6-piperidin-4-yl)butylamino]-6-chloro-s-triazine with N,N'-bis(3-aminopropyl)ethylenediamine The procedure of Example 4 is repeated, except that 2.5 equivalents of 2,4-bis [(1-cyclohexyloxy-2,2,6,6-tetramethylpiperidin-4-yl)butylamino]-6-chloro-s-triazine are used.

This product is also a mixture of isomers including bridged compounds. Analysis by nmr shows that on average between 2.5 and three triazinyl groups are attached to the amine backbone.

The $T_g$ for this product is 109°–116° C. as measured by DSC.

EXAMPLE 6
Reaction of 2,4-bis[(1-cyclohexyloxy-2,2,6,6-piperidin-4-yl)butylamino]-6-chloro-s-triazine with N,N'-bis(3-aminopropyl)ethylenediamine The procedure of Example 4 is repeated, except that 2.0 equivalents of 2,4-bis [(1-cyclohexyloxy-2,2,6,6-tetramethylpiperidin-4-yl)butylamino]-6-chloro-s-triazine are used and the reaction is carried out at 120° C. over five hours.

This product is a mixture of isomers including bridged compounds. Analysis by nmr shows that on average two triazinyl groups are attached to the amine backbone as expected.

The $T_g$ for this product is 101°–114° C. as measured by DSC.

EXAMPLE 7
Purification of the Reaction product of 2,4-bis[(1-cyclohexyloxy-2,2,6,6-piperidin-4-yl)butylamino]-6-chloro-s-triazine with N,N'-bis(3-aminopropyl)ethylenediamine A portion of the product mixture obtained in Example 4 is dissolved in toluene and passed through a column of Phenomenex™ (10 microns) with toluene as the eluent. Fractions are collected and analyzed by gel permeation chromatography. Material having a molecular weight distribution consistent with tris-substituted product is isolated by evaporating the solvent.

EXAMPLE 8
Reaction of Pure 2,4-bis[(1-cyclohexyloxy-2,2,6,6-piperidin-4-yl)butylamino]-6-chloro-s-triazine with N,N'-bis(3-aminopropyl)ethylenediamine

Step 1
Tributyltin hydride is added to a solution of excess 1-oxyl-2,2,6,6-tetramethylpiperidin-4-one and cyclohexyl iodide in chlorobenzene. The mixture is passed through silica gel with heptane/ethyl acetate to obtain 1-cyclohexyloxy-2,2,6,6-tetramethylpiperidin-4-one, which is free of any bis(4-oxo-2,2,6,6-tetramethylpiperidin-1-yloxy)cyclohexane bridged material.

Step 2
A mixture of the compound prepared in step 1 above, n-butylamine, methanol and 5% platinum-on-carbon catalyst is hydrogenated (50 psi, 25° C.). The catalyst is removed by filtration, and the filtrate is evaporated to afford 4-butylamino-1-cyclohexyloxy-2,2,6,6-tetramethylpiperidine.

Step 3
Two equivalents of the compound prepared in step 2 are added to a mixture of cyanuric chloride and xylene at 40° C. Sodium hydroxide is added, and the mixture is heated to 65° C. till the reaction is complete. The reaction mixture is cooled, and water is added. The organic layer is washed with dilute acid, water, dried, and evaporated to afford 2,4-bis[(1-cyclohexyloxy-2,2,6,6-tetramethylpiperidin-4-yl)butylamimno]-6-chloro-s-triazine.

By its method of preparation, this intermediate is clearly not a mixture of compounds such as may be the case with the intermediate made in Example 1.

Step 4
A mixture of N,N'-bis(3-aminopropyl)ethylenediamine and 3.0 equivalents of the compound prepared in step 3 is reacted according to the procedure in Example 4.

EXAMPLE 9
Reaction of 2,4-bis[(1-octyloxy-2,2,6,6-piperidin-4-yl)butylamino]-6-chloro-s-triazine with N,N'-bis(3-aminopropyl)ethylenediamine A mixture of N,N'-bis(3-aminopropyl)ethylenediamine, 3 equivalents of 2,4-bis[(1-octyloxy-2,2,6,6-tetramethylpiperidin-4-yl)butylamino]-6-chloro-s-triazine prepared in Example 2 as a solution in octane, and 20% aqueous sodium hydroxide solution is heated at 120° C. until the reaction is complete. The reaction mixture is cooled, the organic layer is washed with water till neutral, and solvent is evaporated to afford the product mixture.

The nmr analysis is consistent with the expected product of this reaction.

EXAMPLE 10

Reaction of 2,4-bis[(1-methoxy-2,2,6,6-piperidin-4-yl)butylamino]-6-chloro-s-triazinie with N,N'-bis(3-aminopropyl)ethylenediamine A mixture of N,N'-bis(3-aminopropyl)ethylenediamine, 3 equivalents of 2,4-bis[(1-methoxy-2,2,6,6-tetramethylpiperidin-4-yl)butylamino]-6-chloro-1,3,5-triazine a solution in cyclohexane, and 20% aqueous sodium hydroxide solution is heated at 120° C. until the reaction is complete. The reaction mixture is cooled, the organic layer is washed with water till neutral, and solvent is evaporated to afford the product mixture.

EXAMPLE 11

Fiber grade polypropylene, containing 0.05% by weight of calcium stearate and 0.05% by weight of the hydroxylamine made by the direct oxidation of N,N-di(hydrogenated tallow)amine is dry blended with the test additives and then melt compounded at 234° C. (450° F.) into pellets. The pelletized fully formulated resin is then spun at 246° C. (475° F.) into fiber using a Hills laboratory model fiber extruder. The spun tow of 41 filaments is stretched at a ratio of 1:3.2 to give a final denier of 615/41.

Socks are knitted from the stabilized polypropylene fiber on a Lawson-Hemphill Analysis Knitter and exposed in an Atlas Xenon -Arc WeatherOmeter using SAE J1885 Interior Automotiveconditions at 89° C. bpt, 0.55 kW/cm² at 340 nm with no spray cycle. Failure in this test is deterrnined by the observation of the physical failure of the sock when it is "scratched" with a blunt glass rod. The longer it takes for this catastrophic failure to occur, the more effective is the stabilizer system.

The control socks containing, none of the instant compound fail after 200 hours exposure while the sock containing 0.25% by weight of the instant compound mixture of Example 4 or containing 0.25% by weight of the compound of Example 3 fail after 700 hours of exposure. The sock containing 0.5% by weight of the instant compound of Example 4 fail after 1000 hours; while socks with 0.75% by weight of the compound of Example 4 have not failed after 1000 hours exposure.

EXAMPLE 12

Other socks of propylene fiber as prepared in Example 11 are exposed in a Blue M forced draft oven at 120° C. Failure is determined by the criterion set forth in Example 11. The longer it takes for the catastrophic failure to occur, the more effective is the stabilizing system.

The socks containing the instant compounds exhibit good thermal stabilization efficacy.

EXAMPLE 13

Film grade polyethylene is dry blended with approximately 10% by weight of the test additives and then melt compounded at 200° C. into "Masterbatch" pellets. The "Masterbatch" is dry blended with polyethylene resin to get the desired final stabilizer concentration. This stabilized fully formulated resin is then blown at 200° C. into a 150 micron thick film on a DOLCI film line.

The blown films are exposed in an Atlas Xenon-Arc WeatherOmeter according to ASTM G26 at 63° C. bpt, 0.35 W/m² at 340 nm with no spray cycle. Films are tested periodically for any change in elongation using an Instron 112 tensile tester. Failure in this test is determined by observation of the loss of % elongation in the film. The longer it takes for this loss to occur, the more effective is the stabilizer system.

The films containing the instant compound mixture show good light stabilizing efficacy.

EXAMPLE 14

Molded test specimens are prepared by injection molding thermoplastic olefin (TPO) pellets containing a pigment, a phosphite, a phenolic antioxidant or hydroxylamine, a metal stearate, a UV absorber or a hindered amine stabilizer or the hindered amine compounds of formulas I, II, IIA and III; or a mixture of hindered amine and UV absorber.

Pigmented TPO pellets are prepared from pure pigment or pigment concentrate, stabilizers, coadditives and commercially available thermoplastic olefin by mixing the components in a Superior/MPM 1" single screw extruder with a general all-purpose screw (24:1 L/D) at 400° F. (200° C.), cooled in a water bath and pelletized. The resulting formulated pellets are molded into 60 mil (0.006 inch) thick 2"×2" plaques at about 375° F. (190° C.) on a BOY 30M Injection Molding Machine.

Pigmented TPO formulation composed of polypropylene blended with a ribber modifier where the rubber modifier is an in-situ reacted copolymer or blended product containing copolymers of propylene and ethylene with or without a ternary component such as ethylidene norbornene are stabilized with a base stabilization system consisting of an N,N-dialkylhydroxylamine or a mixture of hindered phenolic antioxidant and an organophosphorus compound.

All additive and pigment concentrations in the final formulations are expressed as weight percent based on the resin.

The test formulations contain thermoplastic olefin pellets and one or more of the following components:

0.0–2.0% pigment
0.0–50.0% talc
0.0–0.5% phosphite
0.0–1.25% phenolic antioxidant
0.0–0.1% hydroxylamine
0.0–0.5% calcium stearate
0.0–1.25% UV absorber
0.0–1.25% hindered amine stabilizer The components are dry blended in a tumble dryer prior to extrusion and molding.

Test plaques are mounted in metal frames and exposed in an Atlas Ci65 Xenon Arc WeatherOmeter at 70° C. black panel temperature, 0.55 W/m² at 340 nm and 50% relative humidity with intermittent light/dark cycles and water spray according to the Society of Automotive Engineers (SAE J 1960) test procedure. Specimens are tested at approximately 625 kilojoule intervals by performing color measurements on an Applied Color Systems spectrophotometer by reflectance mode according to ASTM D 2244-79. Data collected include delta E, L*, a* and b* values. Gloss measurements are conducted on a BYK-GARDNER Haze/Gloss Meter at 60° according to ASTM D523

UV Exposure Testing—Test specimens exposed to UV radiation exhibit exceptional resistance to photodegradation when stabilized with light stabilizer systems comprised of a combination of a benzotriazole UV absorber and the hindered amine compounds of formula I, II, IIA and III.

The stabilized samples specifically show improved gloss retention compared to the prior art stabilizer systems. Resistance to color change upon UV exposure is also enhanced. Polymer blends containing an unsaturated ternary component, such as EPDM blends, especially show enhanced properties when stabilized by the instant systems.

In all cases, the light stabilized formulations show much greater resistance to photodegradation than unstabilized specimens which fail quickly under UV exposure conditions as outlined above.

| Formulation** | ΔE hours 0 | ΔE hours 1868 | gloss* hours 0 | gloss* hours 1868 | % gloss retention hours 0 | % gloss retention hours 1868 |
|---|---|---|---|---|---|---|
| HALS A (0.2%) + HALS B (0.2%) | 0.0 | 7.9 | 74.5 | 21.4 | 100 | 28.7 |
| HALS C (0.2%) + HALS of Example 4 (0.2%) | 0.0 | 4.6 | 79.4 | 72.2 | 100 | 90.9 |

*at 60°
**HALS A is bis(2,2,6,6-tetramethylpiperidin-4-yl) sebacate.
HALS B is the polycondensation product of 4,4'-hexamethylene-bis(amino-2,2,6,6-tetra-methylpiperidine) and 2,4-dichloro-6-tert-octylamino-s-triazine.
HALS C is bis(1-octyloxy-2,2,6,6-tetramethylpiperidin-4-yl) sebacate.

The final formulation contains 0.25% of Pigment Red 177, 0.05% of neopentanetetrayl tetrakis(3,5-di-tert-butyl-4-hydroxyhydrocinnamate), 0.05% of tris(2,4-di-tert-butylphenyl) phosphite and 0.2% of 2-(2-hydroxy-3,5-di-tert-amylphenyl)-2H-benzotriazole. Samples are 60 mil thick 2"×2" injection molded plaques. The UV exposures are conducted under exterior automotive conditions according to SAE J 1960 specifications.

EXAMPLE 15a

Film grade polyethylene is dry blended with 10% loading of the test additives and then melt compounded at 200° C. into master batch pellets. The master batch pellets are dry blended with the polyethylene resin to get the final stabilizer concentration. The fully formulated resin is then blown at 200° C. into a 150 micron thick film using a DOLCI film line.

The resulting films are exposed on a greenhouse on galvanized iron backing. Treatment includes applications of pesticides on a regular basis (i.e. sodium N-methyl-dithiocarbamate, VAPAM® every six months and SES-METRIN® every month). Performance is measured by monitoring the percent residual elongation. Failure is defined as the time to a 50% loss of original elongation.

The control film containing 0.4% by weight of the polycondensation product of 4,4'-hexamethylene-bis(amino-2,2,6,6-tetramethylpiperidine) and 2,4-dichloro- 6-tert-octylamino-s-triazine fails after 160 KLYS greenhouse exposure. The film containing 0.4% by weight of the instant compound of Example 3 fails only after 300 KLYS exposure. These results show the resistance to pesticides of the instant compounds of formula I, II, IIA and III.

EXAMPLE 15b

Master batch pellets prepared as described in Example 15a are dry blended into polyethylene resin to get the final stabilizer cocentration. The fully formulated resin is then blown at 200° C. into a 25 micron thick film using a DOLCI film line.

The resulting films are exposed on a soil to simulate agricultural mulch film conditions. Treatment includes exposure to methyl bromide fuimigant for three days at 60 g/m$^3$. Performance is measured by monitoring the time to physical embrittlement.

The control containing 1.2% by weight of the polycondensation product of 4,4'-hexamethylene-bis(amino-2,2,6,6-tetramethylpiperidine) and 2,4-dichloro-6-tert-octylamino-s-triazine fails after 70 KLYS outdoor exposure. The film containing 1.2% by weight of instant compound of Example 3 is still intact after 110 KLYS exposure. These results show the resistance of the instant compounds of formula I, II, IIA and III to fumigants.

EXAMPLE 16

Greenhouse film samples are prepared as described in Example 15, but in addition to the instant compounds of formula I, II, IIA and III also contain a metal stearate or a metal oxide. Typical formulations contain from 0.05 to 2% by weight of the instant hindered amines, 0.05 to 0.5% of a metal stearate such as calcium oxide, and 0.05 to 0.5% of a metal oxide such as zinc oxide or magnesium oxide.

Effectiveness is monitored as described in Example 15. The films containing the instant hindered amine compounds exhibit good light stability.

EXAMPLE 17

Polypropylene fiber is prepared as described in Example 11. In addition to the instant hindered amine compounds of formulas I, II, IIA and III, selected halogenated flame retardants are also included in the formulation. The flame retardants are tris(3-bromo-2,2-bis(bromomethyl)propyl) phosphate, decabromodiphenyl oxide, ethylene bis-(tetrabromophthalimide), or ethylene bis-(dibromo-norbornanedicarboximide).

Using the criterion for light stabilization described in Example 11, the socks knitted from the polypropylene fiber containing the instant hindered amines exhibit good light stability.

EXAMPLE 18

Molding grade polypropylene is dry blended with test additives and then melt compounded into pellets. In addition to the instant hindered amine compounds of formulas I, II, IIA and III, selected flame retardants are also included. The flame retardants are tris(3-bromo-2,2-bis(bromomethyl)propyl) phosphate, decabromodiphenyl oxide, ethylene bis-(tetrabromophthalimide), or ethylene bis-(dibromo-norbornanedicarboximide). The pelletized fully formulated resin is then injection molded into test specimens using a Boy 50M laboratory model injection molder.

Test plaques are mounted in metal frames and exposed in an Atlas Ci65 Xenon Arc Weather-Ometer with intermittent light/dark cycles and water spray following the ASTM G26 test procedure. Specimens are tested at periodic intervals for changes in tensile properties. Failure in this test is determined by the observation of the loss of tensile properties. The longer it takes for the loss in properties to occur, the more effective is the stabilizer system.

The test samples containing the instant hindered amine compounds exhibit good light stabilization properties.

EXAMPLE 19

Molded test specimens are prepared by injection molding thermoplastic olefin (TPO) pellets as described in Example 14. In addition to the instant hindered amines of formulas I, II, IIA and III, selected flame retardants are also included in the test specimens. The flame retardants are tris(3-bromo-2,2-bis(bromomethyl)propyl) phosphate, decabromodiphenyl oxide, ethylene bis-(tetrabromophthalimide), or ethylene bis-(dibromo-norbornanedicarboximide).

The samples including the instant hindered amines exhibit good light stabilizing activity.

EXAMPLE 20

Film grade polyethylene is compounded and blown into film at 200° C. as described in Example 13 using a DOLCI film line. In addition to the instant hindered amines of formulas I, II, IIA and III, selected flame retardants are included in the formulation. The flame retardants are tris(3-bromo-2,2-bis(bromomethyl)propyl) phosphate, decabromodiphenyl oxide, ethylene bis-(tetrabromophthalim ide), or ethylene bis-(dibromo-norbornanedicarboximide).

When tested for light stabilizing activity as described in Example 13, the films containing the instand hindered amines exhibit good stabilization.

EXAMPLE 21

Molded test specimens are prepared by injection molding thermoplastic olefin (TPO) pellets containing the instant hindered amine compounds of formulas I, II, IIA and III, pigments and other coadditives as described in Example 14.

The test specimens are painted with one-pack paint systems and tested for TPO/paint interactions. Before painting, the test specimens are first wiped with isopropanol and air blasted to remove any dust. After a five minute flash, these specimens are coated with the adhesion promoter, then the base coat, and then optionally a clear coat. Typical film thickness of these various coatings are 0.1–0.3 mils for the adhesion promoter, 0.6–0.8 mils for the base coat, and 1.2–1.5 mils for the clear coat. After painting, the specimens are cured in an over at 120° C. for 30 minutes.

Samples are tested to evaluate the TPO/paint interactions as follows: In the initial adhesion test, a clear cellophane adhesive tape is used to pull on a 3 mm cross hatched paint surface or; in the humidity test, the painted plaques are exposed for 240 hours at 38° C. in an atmosphere having 98% relative humidity. The blister rating is tested by visual observation according to ASTM D 714.

The samples containing the instant hindered amine compounds exhibit good TPO/paint interaction properties as determined by the criteria above.

EXAMPLE 22

Polyolefin resins including polypropylene, polyethylene homopolymner, polyolefin copolymer, or thermoplastic olefin (TPO) are dry blended with the instant hindered amine compounds of formulas I, I, IIA and III and then Melt Compounded into pellets. The pelletized fully formulated resin is then processed into a useful article such as extrusion into fiber; blown or cast extrusion into film; blow molded into bottles; injection molded into molded articles; thermoformed into molded articles; extruded into wire and cable housing; or rotational molded into hollow articles.

The materials containing the instant hindered amine compounds exhibit stability against the deleterious effects of UV light and thermal exposure.

EXAMPLE 23

Articles prepared according to Example 22 which additionally contain selected organic pigments as well as the instant compounds of formulas I, II, IIA and III also exhibit stability against the deleterious effects of actinic light and thermal exposure.

EXAMPLE 24

Articles prepared according to Example 22 which additionally contain a hindered phenolic antioxidant selected from the group consisting of neopentanetetrayl tetrakis-(3, 5-di-tert-butyl-4-hydroxyhydrocinnamate, octadecyl 3,5-di-tert-butyl-4-hydroxyhydrocinnamate, 1,3,5-trimethyl-2,4,6-tris(3,5,-di-tert-butyl-4-hydroxybenzyl)benzene, 1,2-bis(3, 5-di-tert-butyl-4-hydroxyhydrocinnamoyl)hydrazine, calcium [bis(monoethyl 3,5-ditert-butyl-4-hydroxybenzyl) phosphonate], 1,3,5-tris(3,5-di-tert-butyl-4-hydroxybenzyl) isocyanurate and 1,3,5-tris(3-hydroxy-4-tert-butyl-2,6-dimethylbenzyl) isocyanurate, as well as the instant compounds of formulas I, II, IIA and III also exhibit stability against the deleterious effects of actinic light and thermal exposure.

EXAMPLE 25

Articles prepared according to Example 22 which additionally contain an organophosphorus stabilizer selected from the group consisting of tris(2,4-di-tert-butylphenyl) phosphite, bis(2,4-di-tert-butyl-6-methylphenyl) ethyl phosphite, 2,2',2"-nitrilo-[triethyl-tris-(3,3',5,5'-tetra-tert-butyl-1,1'-biphenyl-2,2'-diyl) phosphite], tetrakis(2,4-di-butylphenyl) 4,4'-biphenylenediphosphonite, tris (nonylphenyl) phosphite, bis(2,4-di-tert-butylphenyl) pentaerythrityl diphosphite, 2,2'-ethylidenebis(2,4-di-tert-butylphenyl) fluorophosphite and 2-butyl-2-ethylpropan-1, 3-diyl 2,4,6-tri-tert-butylphenyl phosphite as well as the instant compounds of formulas I, II, IIA and III also exhibit stability against the deleterious effects of actinic light and thermal exposure.

EXAMPLE 26

Articles prepared according to Example 22 which additionally contain a benzofuranone stabilizer which is 5,7-di-tert-butyl-3-(3,4-dimethylphenyl)-2H-benzofuran-2-one, as well as the instant compounds of formulas I, II, IIA and III also exhibit stability against the deleterious effects of UV light and thermal exposure.

EXAMPLE 27

Articles prepared according to Example 22 which additionally contain a dialkylhydroxylamine stabilizer which is N,N-dialkylhydroxylamine made by the direct oxidation of N,N-di(hydrogenated tallow)amine as well as the inistant compounds of formulas I, II, IIA and III also exhibit stability against the deleterious effects of actinic light and thermal exposure.

EXAMPLE 28

Articles prepared according to Example 22 which additionally contain other hindered amine stabilizers selected from the group consisting, of bis(2,2,6,6-tetramethylpiperidin-4-yl) sebacate, the polycondensation product of 1-(2-hydroxyethyl)-2,2,6,6-tetramethyl-4-hydroxypiperidine and succinic acid, N.N',N",N'"-tetrakis[4, 6-bis(butyl-1,2,2,6,6-pentamethylpiperidin-4-yl)amino-s-triazin-2-yl]-1,10-diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'- hexamethylenebis(amino-2,2,6,6-tetramethylpiperidine) and 2,4-dichloro-6-morpholino-s-triazine, 2,2,6,6-tetramethylpiperidin-4-yl octadecanoate, 3-dodecyl-1-(1-acetyl-2,2,6,6-tetramethylpiperidin-4-yl)-pyrrolidin-2,5-dione, 1,3,5-tris{N-cyclohexyl-N-[2-(2,2,6,6-tetramethylpiperazin-3-on-4-yl)ethyl]amino}-s-triazine, poly[methyl 3-(2,2,6,6-tetramethylpiperidin-4-yloxy)propyl]siloxane, the polycondensation product of 2,4-dichloro-6-(2,2,6,6-tetramethylpiperidin-4-yl)butylamino)-s-triazine and 2,2'ethylene-bis{[2,4-(2,2,6,6-tetramethylpiperidin-4-yl)butylamino-s-triazin-6-yl]aminotrimethyleneamino} as well as the instant compounds of formulas I, II, IIA and III also exhibit stability against the deleterious effects of actinic light and thermal exposure.

EXAMPLE 29

Articles prepared according to Example 22 which additionally contain other N-hydrocarbyloxy substituted hindered amines selected from the group consisting of bis(1-octyloxy-2,2,6,6-tetramethylpiperidin-4-yl) sebacate, bis(1-octyloxy-2,2,6,6-tetramethylpiperidin-4-yl)adipate, bis(1-cyclohexyloxy-2,2,6,6-tetramethylpiperidin-4-yl) adipate, bis(1-cyclohexyloxy-2,2,6,6-tetramethylpiperidin-4-yl) sebacate, and 1-cyclohexyloxy-2,2,6,6-tetramethylpiperidin-4-yl octadecanoate as well as the instant compounds of formulas I, II, IIA and III also exhibit stability against the deleterious effects of actinic light and thermal exposure.

EXAMPLE 30

Articles prepared according to Example 22 which additionally contain a o-hydroxyphenyl-2H-benzotriazole, a hydroxyphenyl benzophenone or a o-hydroxyphenyl-s-triazine UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl4-hydroxybenzoate, 2-hydroxy-4-n-octyloxybenzophenone and 2,4-bis(2,4-dimethyphenyl)-6-(2-hydroxy-4-octyloxyphenyl)-s-triazine as well as the instant compounds of formulas 1, II, IIA and III also exhibit stability against the deleterious effects of UV light and thermal exposure.

What is claimed is:

1. A composition stabilized against thermal, oxidative or light-induced degradation which comprises, (a) an organic material subject to thermal, oxidative or light-induced degradation, and (b) an effective stabilizing amount of a mixture of N,N',N"'-tris{2,4-bis[(1-hydrocarbyloxy-2,2,6,6-tetramethylpiperidin-4-yl)alkylamino]-s-triazin-6-yl}-3,3'-ethylenediiminodipropylamine; N,N',N"-tris{2,4-bis-[(1-hydrocarbyloxy-2,2,6,6-tetramethylpiperidin-4-yl)alkylamino]-s-triazin-6-yl}-3,3'-ethylenediiminodipropylamine and bridged derivatives as described by formulas I, II, IIA and III $R_1NH-CH_2CH_2CH_2NR_2CH_2CH_2NR_3CH_2CH_2CH_2NHR_4$ (I)

$T-E_1-T_1$ (II)

$T-E_1$ (IIA)

$G-E_1-G_1-E_1-G_2$ (III)

where in the tetraamine of formula I, $R_1$ and $R_2$ are the s-triazine moiety E; and one of $R_3$ and $R_4$ is the s-triazine moiety E with the other of $R_3$ and $R_4$ being hydrogen, E is

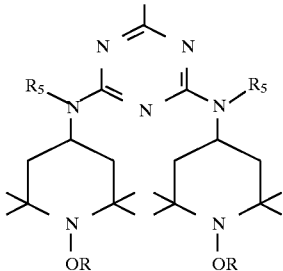

R is methyl, cyclohexyl or octyl, $R_5$ is alkyl of 1 to 12 carbon atoms, where in the compound of formula II or IIA when R is cyclohexyl or octyl T and $T_1$ are each a tetraamine substituted by $R_1$–$R_4$ as defined for formula I, where (1) one of the s-triazine moieties E in each tetraamine is replaced by the group $E_1$ which forms a bridge between the two tetraamines T and $T_1$, $E_1$ is

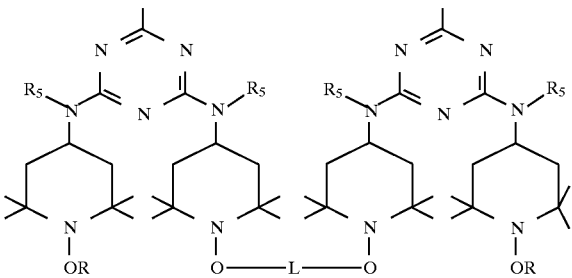

or (2) the group $E_1$ can have both termini in the same tetraamine T as in formula IIA where two of the E moieties of the tetraamine are replaced by one $E_1$ group, or (3) all three s-triazine substituents of tetraamine T can be $E_1$ such that one $E_1$ links T and $T_1$ and a second $E_1$ has both termini in tetraamine T, L is cyclohexanediyl or octanediyl;

where in the compound of formula III

G, $G_1$ and $G_2$ are each tetraamines substituted by $R_1$–$R_4$ as defined for formula I, except that G and $G_2$ each have one of the s-triazine moieties E replaced by $E_1$, and $G_1$ has two of the triazine moieties E replaced by $E_1$, so that there is a bridge between G and $G_1$ and a second bridge between $G_1$ and $G_2$, which mixture is prepared by reacting two to four equivalents of 2,4-bis[(1-hydrocarbyloxy-2,2,6,6-piperidin-4-yl)butylamino]-6-chloro-s-triazine with one equivalent of N,N'-bis(3-amino-propyl)ethylenediamine.

2. A composition according to claim 1 wherein the organic material is a natural, semi-synthetic or synthetic polymer.

3. A composition according to claim 1 wherein the organic material is a thermoplastic polymer.

4. A composition according to claim 1 wherein the organic material is a polyolefin, a thermoplastic olefin or a polycarbonate.

5. A composition according to claim 4 wherein the organic material is a polyolefin.

6. A composition according to claim 5 wherein the polyolefin is polyethylene or polypropylene.

7. A composition according to claim 1 wherein in the E and $E_1$ moieties of the compounds of component (b), R is cyclohexyl or octyl, and $R_5$ is n-butyl.

8. A composition according to claim 1 wherein the effective stabilizing amount is 0.01 to 5% by weight of the stabilized composition.

9. A mixture of N,N',N'''-tris{2,4-bis[(1-hydrocarbyloxy-2,2,6,6-tetramethylpiperidin-4-yl)alkylamino]-s-triazin-6-yl}-3,3'-ethylenediiminodipropylamine; N,N',N''-tris-{2,4-bis[(1-hydrocarbyloxy-2,2,6,6-tetramethylpiperidin-4-yl) alkylamino]-s-triazin-6-yl}-3,3'-ethylenediiminodipropylamine, and bridged derivatives as described by formulas I, II, IIA and III

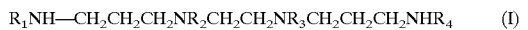  (I)

  (II)

  (IIA)

  (III)

where in the tetraamine of formula I, $R_1$ and $R_2$ are the s-triazine moiety E; and one of $R_3$ and $R_4$ is the s-triazine moiety E with the other of $R_3$ and $R_1$ being hydrogen, E is

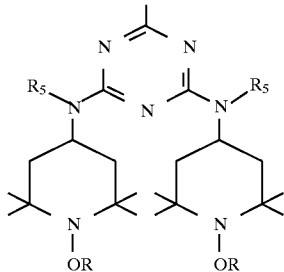

R is methyl, cyclohexyl or octyl, $R_5$ is alkyl of 1 to 12 carbon atoms, where in the compound of formula II or IIA when R is cyclohexyl or octyl, T and $T_1$ are each a tetraamine substituted by $R_1$–$R_4$ as defined for formula I, where (1) one of the s-triazine moieties E in each tetraamine is replaced by the group $E_1$ which forms a bridge between the two tetraamines T and $T_1$.

$E_1$ is

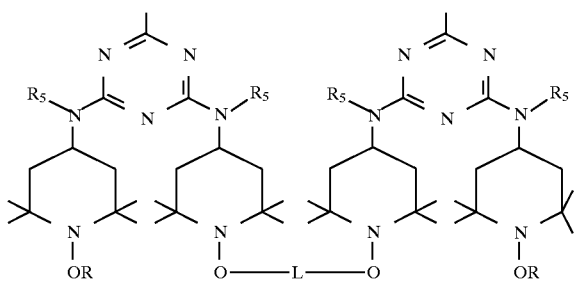

or (2) the group $E_1$ can have both termini in the same tetraamine T as in formula IIA where two of the E moieties of the tetraamine are replaced by one $E_1$ group, or (3) all three s-triazine substituents of tetraamine T can be $E_1$ such that one $E_1$ links T and $T_1$ and a second $E_1$ has both termini in tetraamine T, L is cyclohexanediyl or octanediyl;

where in the compound of formula III

G, $G_1$ and $G_2$ are each tetraamines substituted by $R_1$–$R_4$ as defined for formula I, except that G and $G_2$ each have one of the s-triazine moieties E replaced by $E_1$, and $G_1$ has two of the triazine moieties E replaced by $E_1$, so that there is a bridge between G and $G_1$ and a second bridge between $G_1$ and $G_2$, which mixture is prepared by reacting two to four equivalents of 2,4-bis[(1-hydrocarbyloxy-2,2,6,6-piperidin-4-yl)butylamino]-6-chloro-s-triazine with one equivalent of N,N'-bis(3-amino-propyl)ethylenediamine.

10. A mixture according to claim 9 wherein in the E and $E_1$ moieties, R is cyclohexyl or octyl, and $R_5$ is n-butyl.

11. A mixture of N,N',N'''-tris{2,4-bis[(1-cyclohexyloxy-2,2,6,6-tetramethylpiperidin-4-yl)n-butylamino]-s-triazin-6-yl}-3,3'-ethylenediiminodipropylamine; N,N',N''-tris{2,4-bis[(1-cyclohexyloxy-2,2,6,6-tetramethylpiperidin-4-yl)n-butylamino]-s-triazin-6-yl}-3,3'-ethylenediiminodipropylamine and bridged derivatives as described by formulas I, II, IIA and III according to claim 9.

12. A mixture of N,N',N'''-tris{2,4-bis[(1-octyloxy-2,2,6,6-tetramethylpiperidin-4-yl)n-butylamino]-s-triazin-6-yl}-3,3'-ethylenediiminodipropylamine; N,N',N''-tris-{2,4-bis[(1-octyloxy-2,2,6,6-tetramethylpiperidin-4-yl)n-butylamino]-s-triazin-6-yl}-3,3'-ethylenediiminodipropylamine and bridged derivatives as described by formulas I, II, IIA and III according to claim 9.

13. A mixture of N,N',N'''-tris{2,4-bis[(1-methoxy-2,2,6,6-tetramethylpiperidin-4-yl)n-butylamino]-s-triazin-6-yl}-3,3'-ethylenediiminodipropylamine; N,N',N''-tris-{2,4-bis[(1-methoxy-2,2,6,6-tetramethylpiperidin-4-yl)n-butylamino]-s-triazin-6-yl}-3,3'-ethylenediiminodipropylamine and bridged derivatives as described by formulas I, II, IIA and III according to claim 9.

14. A process of making the instant mixture of N,N',N'''-tris{2,4-bis[(1-hydrocarbyloxy-2,2,6,6-tetramethylpiperidin-4-yl)alkylamino]-s-triazin-6-yl}-3,3'-ethylenediiminodipropylamine; N,N',N''-tris{2,4-bis[(1-hydrocarbyloxy-2,2,6,6-tetramethylpiperidin-4-yl) alkylamino]-s-triazin-6-yl}-3,3'-ethylenediiminodipropylamine and bridged derivatives as described by formulas I, II, IIA and III according to claim 9 which comprises reacting two to four equivalents of 2,4-bis[(1-hydrocarbyloxy-2,2,6,6-piperidin-4-yl)butylamino]-6-chloro-s-triazine with one equivalent of N,N'-bis(3-aminopropyl)-ethylenediamine.

15. A process according to claim 14 which comprises reacting 2.5 to three equivalents of the s-triazine with one equivalent of the amine.

16. A process according to claim 14 which comprises reacting three equivalents of the s-triazine with one equivalent of the amine.

17. A process according to claim 14 wherein the hydrocarbyloxy is cyclohexyloxy.

18. A process according to claim 14 wherein the hydrocarbyloxy is octyloxy.

19. A process according to claim 14 wherein the hydrocarbyloxy is methoxy.

20. N,N',N'''-tris{2,4-bis[(1-cyclohexyloxy-2,2,6,6-tetramethylpiperidin-4-yl)-n-butylamino]-s-triazin-6-yl}-3,3'-ethylenediiminodipropylamine.

21. N,N',N''-tris{2,4-bis[(1-cyclohexyloxy-2,2,6,6-tetramethylpiperidin-4-yl)-n-butylamino]-s-triazin-6-yl}-3,3'-ethylenediiminodipropylamine.

22. N,N',N'''-tris{2,4-bis[(1-octyloxy-2,2,6,6-tetramethylpiperidin-4-yl)n-butyl-amino]-s-triazin-6-yl}-3,3'-ethylenediiminodipropylamine.

23. N,N',N''-tris{2,4-bis[(1-octyloxy-2,2,6,6-tetramethylpiperidin-4-yl)n-butyl-amino]-s-triazin-6-yl}-3,3'-ethylenediiminodipropylamine.

24. N,N',N'''-tris{2,4-bis[(1-methoxy-2,2,6,6-tetramethylpiperidin-4-yl)n-butyl-amino]-s-triazin-6-yl}-3,3'-ethylenediiminodipropylamine.

25. N,N',N''-tris{2,4-bis[(1-methoxy-2,2,6,6-tetramethylpiperidin-4-yl)n-butyl-amino]-s-triazin-6-yl}-3,3'-ethylenediiminodipropylamine.

26. A composition according to claim 1 which additionally contains an effective stabilizing amount of at least one coadditive stabilizer selected from the group consisting of the phenolic antioxidants, metal stearates, metal oxides, organophosphorus compounds, furanone antioxidants, hydroxylamines, non-NOR hindered amines, NOR hindered amines and mixtures thereof.

27. A composition according to claim 26 wherein component (a) is a thermoplastic olefin, and the component (b) additionally contains a low molecular NOR hindered amine.

28. A composition according to claim 1 wherein component (a) is an agricultural film which is exposed to pesticides.

29. A composition according to claim 26 wherein component (a) is an agricultural film exposed to pesticides, and component (b) additionally contains a metal stearate and zinc oxide.

30. A composition according to claim 1 wherein component (a) is a polyolefin film, fiber, thick section or thermoplastic olefin article which additionally contains a halogenated flame retardant which is decabromodiphenyl oxide; ethylene bis-(tetrabromo-phthalimide), or ethylene bis-(dibromo-norbornanedicarboximide).

31. A composition according to claim 1 wherein component (a) is a paintable thermoplastic olefin (TPO).

32. A composition according to claim 26 wherein the coadditive stabilizer is a hindered phenolic antioxidant selected from the group consisting of neopentanetetrayl tetrakis(3,5-di-tert-butyl-4-hydroxyhydrocinnamate, octadecyl 3,5-di-tert-butyl-4-hydroxyhydrocinnamate, 1,3,5-trimethyl-2,4,6-tris(3,5,-di-tert-butyl-4-hydroxybenzyl)-benzene, 1,2-bis(3,5-di-tert-butyl-4-hydroxyhydrocinnamoyl)hydrazine, calcium [bis(monoethyl 3,5-ditert-butyl-4-hydroxybenzyl) phosphonate], 1,3,5-tris(3,5-di-tert-butyl-4-hydroxybenzyl) isocyanurate and 1,3,5-tris(3-hydroxy-4-tert-butyl- 2,6-dimethylbenzyl) isocyanurate; or is an organophosphorus stabilizer selected from the group consisting of tris(2,4-di-tert-butylphenyl) phosphite, bis(2,4-di-tert-butyl-6-methylphenyl) ethyl phosphite, 2,2',2''-nitrilo[triethyl-tris-(3,3',5,5'-tetra-tert-butyl-1,1'-biphenyl-2,2'-diyl)phosphite], tetrakis(2,4-di-butylphenyl) 4,4'-biphenylenediphosphonite, tris(nonylphenyl) phosphite, bis(2,4-di-tert-butylphenyl) pentaerythrityl diphosphite, 2,2'-ethylidenebis(2,4-di-tert-butylphenyl) flluorophosphite and 2-butyl-2-ethylpropan-1,3-diyl 2,4,6-tri-tert-butylphenyl phosphite; or is 5,7-di-tert-butyl-3-(3,4-dimethylphenyl)-2H-benzofuran-2-one; or is N,N-dialkylhydroxylamine made by the direct oxidation of N,N-di(hydrogenated tallow)amine; or is a hindered amine selected from the group consisting of bis(2,2,6,6-tetramethylpiperidin-4-yl) sebacate, the polycondensation product of 1-(2-hydroxyethyl)-2,2,6,6-tetramethyl-4-hydroxypiperidine and succinic acid, N.N',N'',N'''-tetrakis[4,6-bis(butyl-1,2,2,6,6-pentamethylpiperidin-4-yl)amino-s-triazin-2-yl]-1,10-diamino-4,7-diazadecane, the polycondensation product of 4,4'-hexamethylenebis(amino-2,2,6,6-tetramethylpiperidine) and 2,4-dichloro-6-tert-octylamino-s-triazine, the polycondensation product of 4,4'-hexamethylenebis(amino-2,2,6,6-tetramethylpiperidine) and 2,4-dichloro-6-morpholino-s-triazine, 2,2,6,6-tetramethylpiperidin-4-yl octadecanoate, 3-dodecyl-1-(1-acetyl-2,2,6,6-tetramethylpiperidin-4-yl)-pyrrolidin-2,5-dione, 1,3,5-tris{N-cyclohexyl-N-[2-(2,2,6,6-tetramethylpiperazin-3-on-4-yl)ethyl]amino}-s-triazine, poly[methyl 3-(2,2,6,6-tetramethylpiperidin-4-yloxy)-propyl]siloxane, the polycondensation product of 2,4-dichloro-6-(2,2,6,6-tetramethylpiperidin-4-yl)butylamino)-s-triazine and 2,2'ethylene-bis{[2,4-(2,2,6,6-tetramethylpiperidin-4-yl)butylamino-s-triazin-6-yl] aminotrimethyleneaminmo}; or is another N-hydrocarbyloxy substituted hindered amines selected from the group consisting of bis(1-octyloxy-2,2,6,6-tetramethylpiperidin-4-yl) sebacate, bis(1-octyloxy-2,2,6,6-tetramethylpiperidin-4-yl) adipate, bis(1-cyclohexyloxy-2,2,6,6-tetramethylpiperidin-4-yl) adipate, bis(1-cyclohexyloxy-2,2,6,6-tetramethylpiperidin-4-yl) sebacate, and 1-cyclohexyloxy-2,2,6,6-tetramethylpiperidin-4-yl octadecanoate; or is a UV absorber selected from the group consisting of 2-(2-hydroxy-3,5-di-α-cumylphenyl)-2H-benzotriazole, 2-(2-hydroxy-5-methylphenyl)-2H-benzotriazole, 5-chloro-2-(2-hydroxy-3,5-di-tert-butylphenyl)-2H-benzotriazole, 2-(2-hydroxy-3,5-di-tert-amylphenyl)-2H-benzotriazole, 2-(2-hydroxy-3-α-cumyl-5-tert-octylphenyl)-2H-benzotriazole, 2,4-di-tert-butylphenyl 3,5-di-tert-butyl4-hydroxybenzoate, 2-hydroxy-4-n-octyloxybenzophenone and 2,4-bis(2,4-dimethyphenyl)-6-(2-hydroxy-4-octyloxyphenyl)-s-triazine; or mixtures thereof.

* * * * *